(12) United States Patent
Park et al.

(10) Patent No.: US 7,567,306 B2
(45) Date of Patent: Jul. 28, 2009

(54) LIQUID CRYSTAL SKI GOGGLES AND METHODS OF MANUFACTURING THE SAME

(75) Inventors: Eui-Yeul Park, Hudson, OH (US); Roy Miller, Akron, OH (US); Tamas Kosa, Hudson, OH (US); Bahman Taheri, Hudson, OH (US)

(73) Assignee: AlphaMicron, Inc., Kent, OH (US)

( * ) Notice: Subject to any disclaimer, the term of this patent is extended or adjusted under 35 U.S.C. 154(b) by 254 days.

(21) Appl. No.: 11/487,079

(22) Filed: Jul. 14, 2006

(65) Prior Publication Data

US 2008/0013000 A1 Jan. 17, 2008

(51) Int. Cl.
G02F 1/1335 (2006.01)
G02C 7/00 (2006.01)
(52) U.S. Cl. .......................... 349/13; 349/14
(58) Field of Classification Search ............... 349/13, 349/14
See application file for complete search history.

(56) References Cited

U.S. PATENT DOCUMENTS 4,300,818 A * 11/1981 Schachar ............... 351/210

2007/0242173 A1 * 10/2007 Blum et al. ............... 349/13

FOREIGN PATENT DOCUMENTS

| EP | 436845 A1 * | 7/1991 |
| JP | 1986-304961 A | 6/1988 |
| JP | 63157128 A * | 6/1988 |

* cited by examiner

Primary Examiner—Michelle R Connelly Cushwa
(74) Attorney, Agent, or Firm—Renner Kenner Greive Bobak Taylor & Weber

(57) ABSTRACT

A goggle includes a lens assembly which comprises a front lens, a rear lens spaced apart from the front lens, and a liquid crystal device disposed on one of the lenses. The goggle includes a frame, which defines an aperture and a peripheral channel. The peripheral channel receives the front lens and the rear lens is positioned rearward of the channel so that the aperture receives the lens assembly. A power unit includes a battery and a drive circuit, wherein the drive circuit is connected to a pair of prongs that are electrically connectable to the liquid crystal device for operation thereof. The power unit provides a master switch connected to the battery to control application of power to the drive circuit, and a state change switch to control application of power from the drive circuit, through the prongs, to the liquid crystal device.

23 Claims, 11 Drawing Sheets

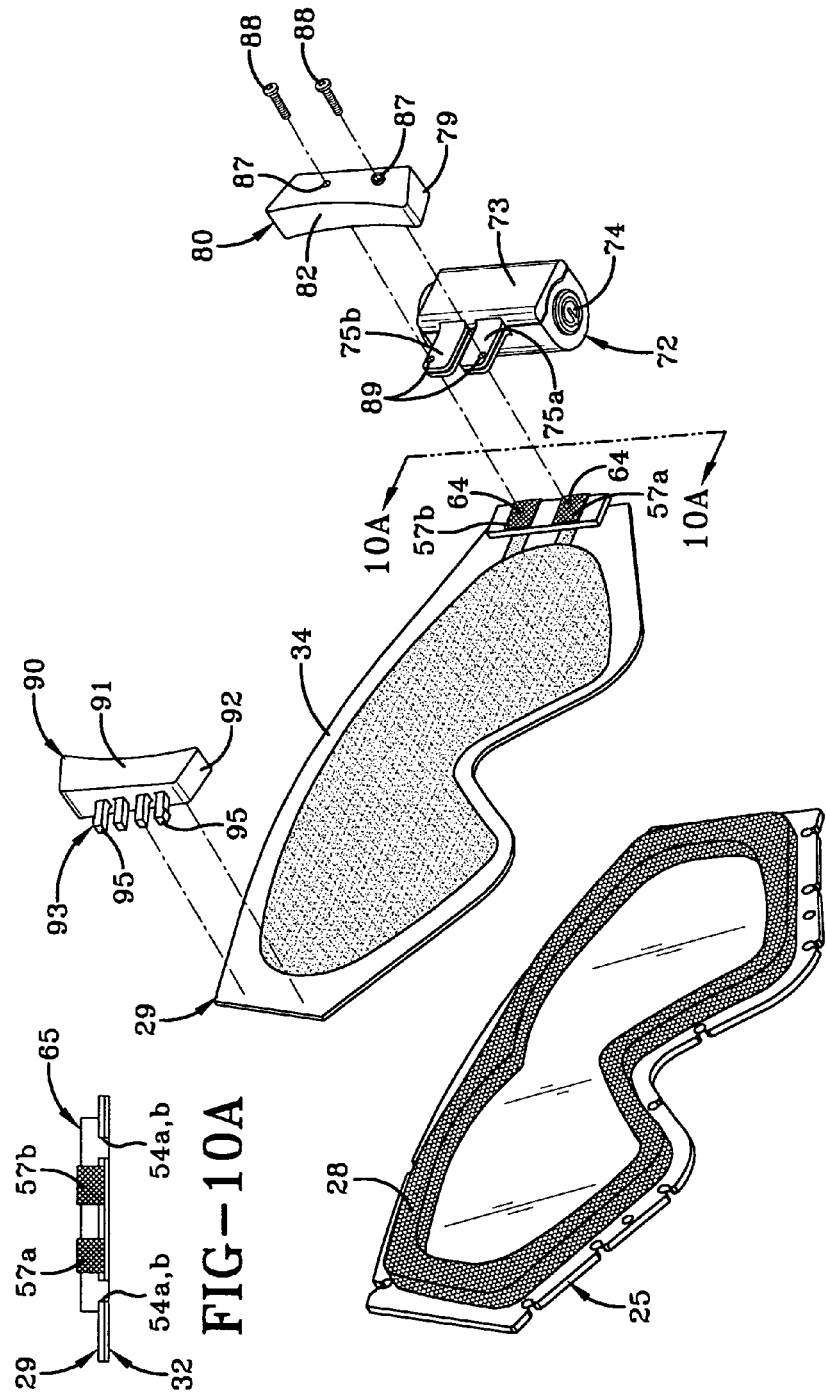

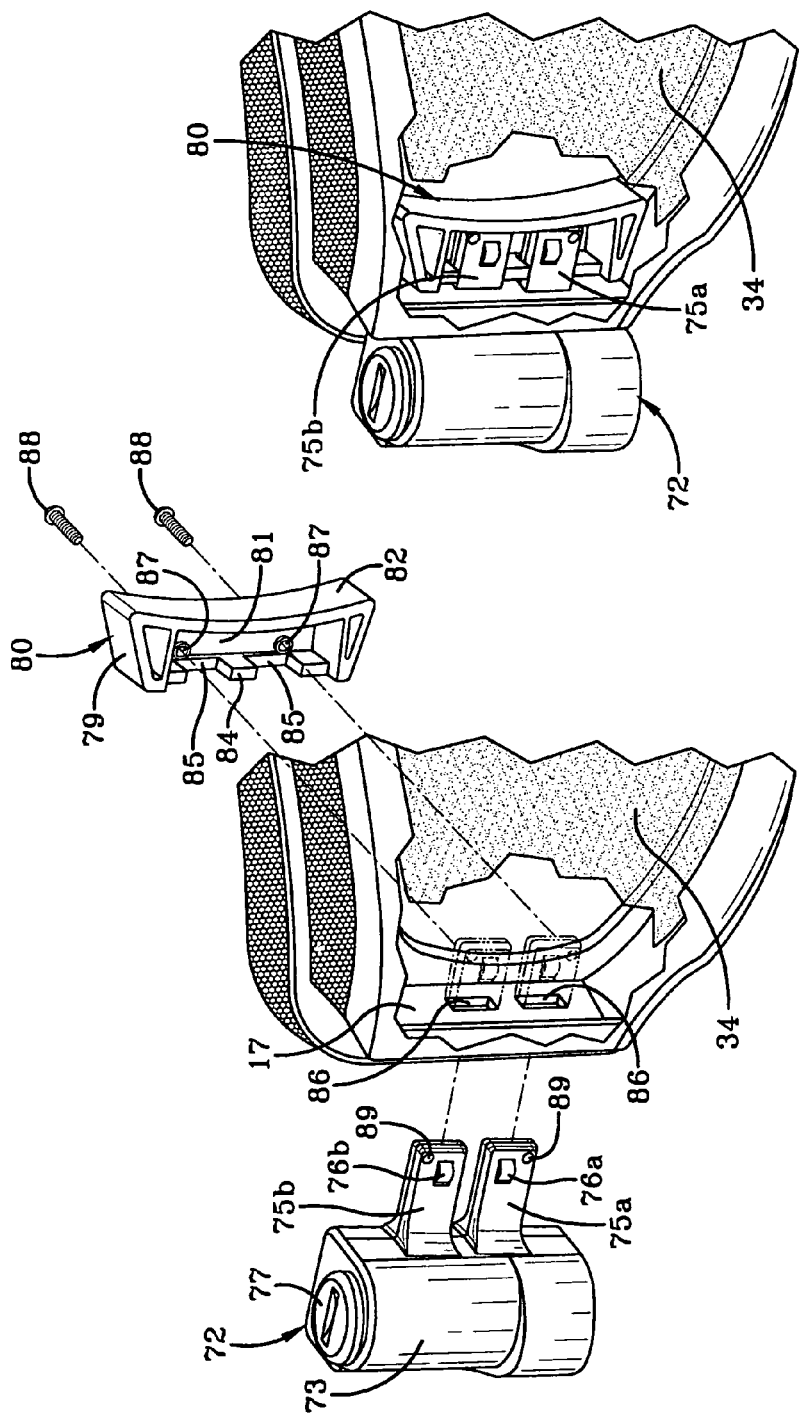

LIQUID CRYSTAL SKI GOGGLES AND METHODS OF MANUFACTURING THE SAME

The present invention relates generally to goggles, and more particularly to ski goggles including a user actuated liquid crystal device.

BACKGROUND OF THE INVENTION

Liquid crystal devices have been developed and used in a variety of applications, from computer displays to industrial uses. These devices are capable of a variety of functions, one of which is the ability to change optical properties with very low power consumption. Specifically, these devices may have a first, unactuated state, and a second actuated state, wherein the application of an electric potential or other physical stimulus causes the device to switch between the states. Removal of the electric potential causes the device to revert to the default state. Depending on the structure of the device, one state is less transparent or darker and one state is more transparent or lighter. Thus, a user may selectively darken the device, and, in the case of eyewear, darken the device that is associated with the eyewear.

Recently, liquid crystal devices have been put to use in outdoor goggles such as ski goggles. It has been found that associating a liquid crystal device with a lens of a ski goggle advantageously allows the user to darken or lighten the tint of the lens depending upon outside conditions. In other words, a user may prefer a darkened lens in bright sun conditions and a lightened lens in overcast or evening conditions. Such goggles are an improvement over prior art tinted lenses, but certain problems were realized in early designs.

Standard ski goggles typically include a front lens exposed to the exterior elements and a rear lens, which is closer to the user's eyes, wherein the front and rear lens are spaced apart by a gasket or the like. The liquid crystal device was disposed proximal the rear lens, facing the front lens. It was found that standard goggle constructions caused strain and stresses on the rear lens which were transferred to the liquid crystal device and, in turn, resulted in failures in the liquid crystal device. Specifically, the rear lens was usually tightly adhered to the gasket which was tightly adhered to the front lens which was held tightly within a peripheral channel. This configuration, while acceptable for normal goggles, caused flexing and other strains on the rear lens which contorted and ultimately led to the failure of some liquid crystal devices. Specifically, the electrodes used to connect an electrical power supply to electrode layers of the liquid crystal device were found to be quite susceptible to the aforementioned contortion, flexing and strains. Breakage of the electrodes results in a failure of the goggle that is very difficult to repair. And it was found that the electrical path between a power unit and the liquid crystal device was fragile and susceptible to failure, particularly in harsh outdoor conditions. Such failures were not easily remedied.

Thus there exists a need in the art to provide a liquid crystal ski goggle which reduces applied stresses on the liquid crystal device and further provides dependable and rugged electrical connection to a power source.

SUMMARY OF THE INVENTION

In light of the foregoing, it is a first aspect of the present invention to provide liquid crystal ski goggles and methods of manufacturing the same.

It is another aspect of the present invention to provide a goggle comprising a frame defining an aperture, the frame providing a peripheral channel about the aperture, a lens assembly comprising a front lens, a rear lens spaced apart from the front lens and a liquid crystal device disposed on one of the lenses, and wherein the peripheral channel receives one of the lenses which does not carry the liquid crystal device.

Yet another aspect of the present invention is to provide a liquid crystal lens assembly for a goggle, comprising a lens adapted to fit within the goggle, the lens having a front surface and a rear surface, a liquid crystal device disposed on one of the surfaces and including opposed first and second substrates, the first substrate having a first conductive layer disposed thereon, the first conductive layer including a first active area and first and second tabs, the second substrate having a second conductive layer disposed thereon, the second conductive layer including a second active area and third and fourth tabs, the first and second active areas being aligned and defining a volume therebetween to receive a liquid crystal material, a first conductive strip disposed between the first and third tabs, a second conductive strip disposed between the second and fourth tabs, and wherein the first conductive strip is electrically connected to the first active area and the second conductive strip is electrically connected to the second active area.

Still another aspect of the present invention is to provide a goggle comprising a frame defining an aperture, the frame having a top edge, a lens assembly received within the aperture and including at least a liquid crystal device, and a power unit electrically connected to the liquid crystal device including a housing positioned outside the frame and a state change button, wherein the state change button is depressible to actuate the liquid crystal device, and wherein the state change button is positioned away from the top edge.

Yet another aspect of the present invention is to provide a power unit that supplies power to a liquid crystal device, comprising a housing, a battery carried by the housing, a drive circuit carried by the housing and connected to the battery, at least one prong extending from the housing, the prong providing at least two electrical leads connected to the drive circuit, a master switch connected to the battery to control application of power to the drive circuit, and a state change switch adapted to control application of power from the at least two electrical leads to the liquid crystal device.

BRIEF DESCRIPTION OF THE DRAWINGS

For a complete understanding of the objects, techniques and structure of the invention, reference should be made to the following detailed description and accompanying drawings wherein:

FIG. 2A is a detailed view of a designated section of FIG. 2 showing the lens assembly carried by the front frame;

FIG. 10 is a rear exploded view of the sub-assembly shown in FIG. 9, a front lens, and a retaining clip according to the present invention;

FIG. 10A is a side view of the support, the rear lens and the liquid crystal device taken along lines 10A-10A of FIG. 10;

FIG. 11 is a partial exploded perspective view showing the power unit, a power unit retainer and the goggle frame with the lenses partially broken away;

FIG. 11A is a partial perspective view of the power unit retained by the power unit retainer in the goggle frame with the lenses partially broken away;

DESCRIPTION OF THE PREFERRED EMBODIMENT

Figure 1:
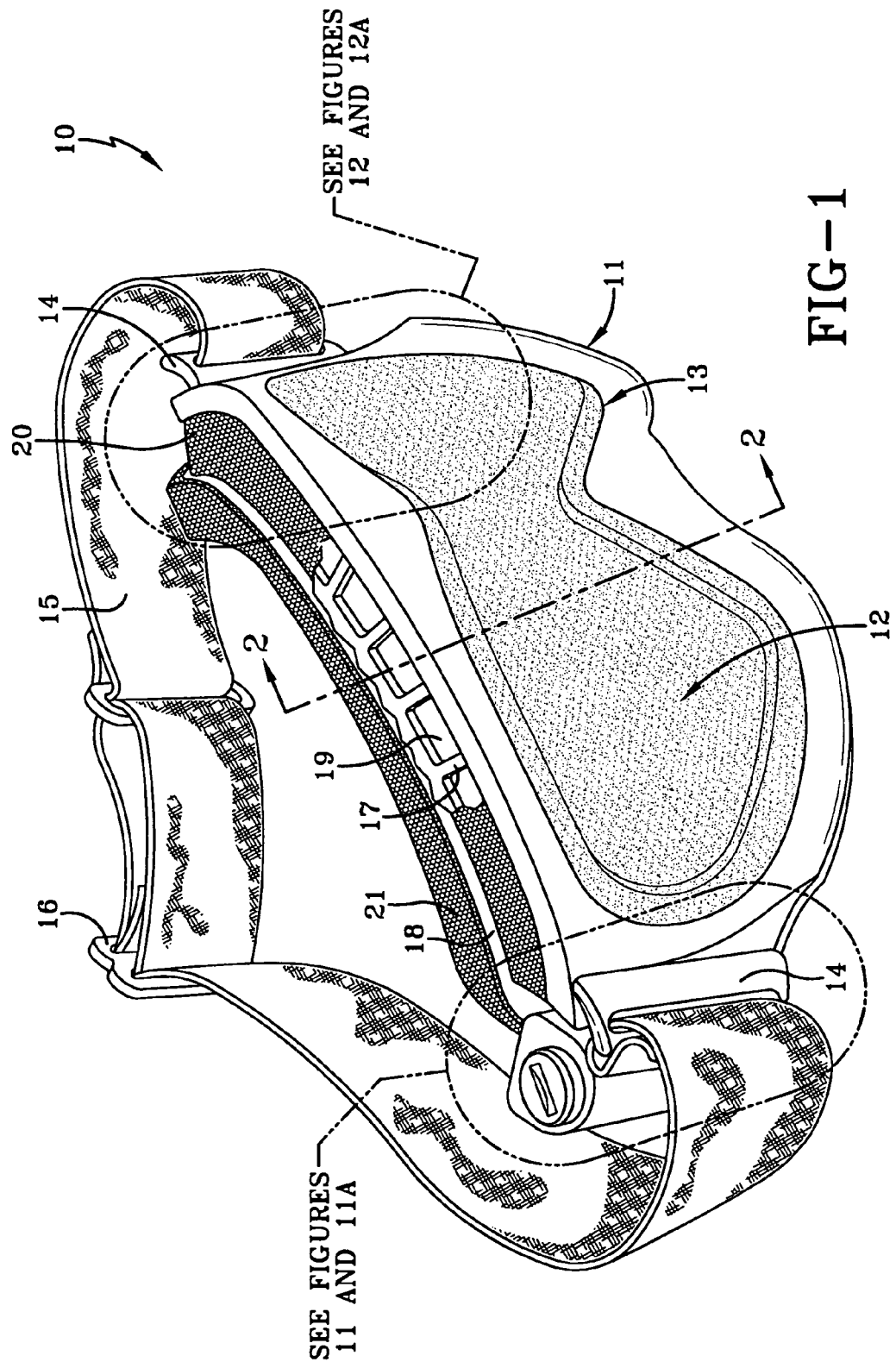
FIG. 1 is an elevated perspective view of a liquid crystal ski goggle made according to the present invention.

A liquid crystal ski goggle made in accordance with the present invention and shown in the drawings is indicated generally by the numeral 10. As used herein, the goggle 10 refers to a single unit or assembly worn by a user. The goggle 10 disclosed in the accompanying figures is adapted particularly for use in outdoor activities such as skiing, but it should be appreciated that the foregoing teachings are applicable to other eyewear applications such as, for example, industrial uses or the like.

As best seen in FIG. 1, goggle 10 includes a front frame 11 which may be composed of a flexible, yet resilient plastic material. Front frame 11 defines an aperture 12 which receives and carries a lens assembly 13, through which a user views his or her surroundings. A strap retainer 14 extends from each opposed end of front frame 11. Each retainer 14 receives an end of a strap 15 therein. Strap 15 may be a flexible fabric and may include adjustors 16 which vary the length depending upon user requirements.

A framework 17 extends rearward from front frame 11 and terminates at a rear frame 18. Rear frame 18 includes a profile which generally matches that of front frame 11. Framework 17 thus joins front and rear frames 11 and 18 and may include a plurality of vents 19 which allow the passage of air therethrough. Further, framework 17 may be covered by a foamed material 20 which partially restricts airflow and performs decorative and insulating functions. The foamed material 20 also prevents debris from entering between the front and rear frames. Likewise, a foam cushion 21 extends rearward from rear frame 18 and is adapted to provide a soft contoured form-fitting surface for a user to place his or her face.

Figure 2:
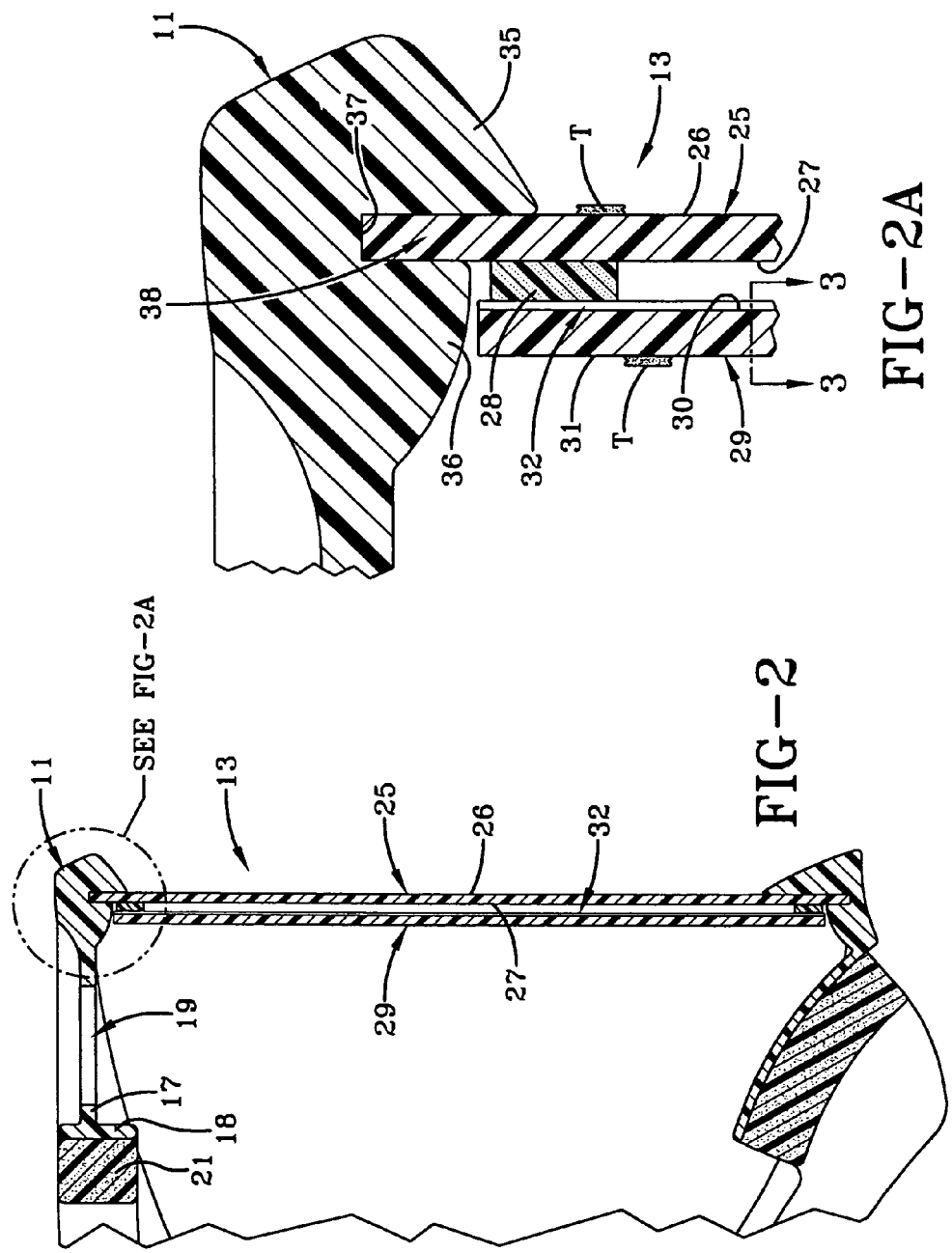
FIG. 2 is a cross-sectional view taken along lines 2-2 of FIG. 1 of the goggle and specifically a lens assembly and a front frame according to the present invention.
Figure 3:
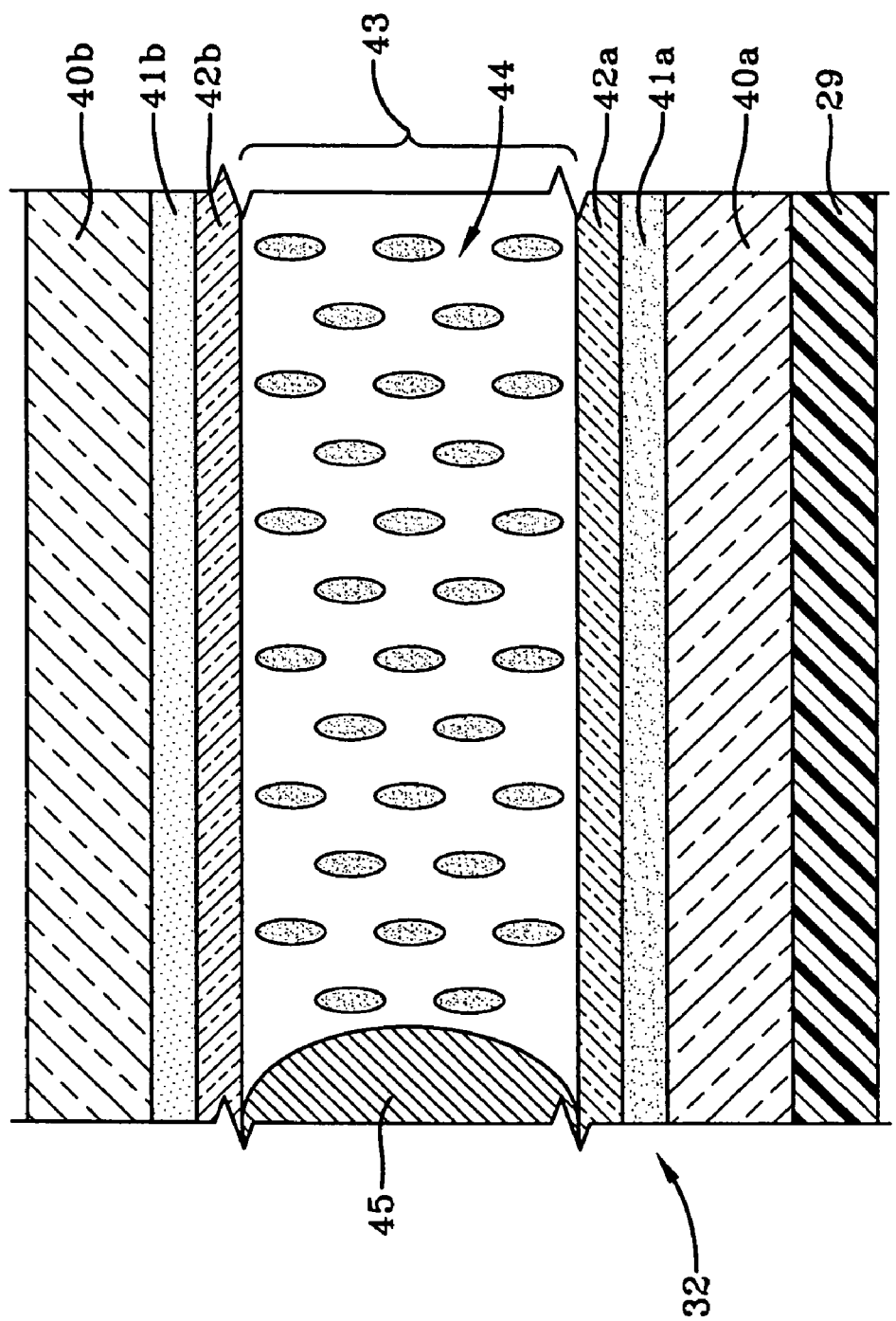
FIG. 3 is a cross-sectional view taken along lines 3-3 of FIG. 2A showing a liquid crystal device carried by the lens assembly.

Referring now to FIGS. 2 and 2A, it can be seen that lens assembly 13 is a multilayer element including a front lens 25 generally in the shape of, but slightly larger than aperture 12. Although any plastic material could be used, front lens 25 is a shatter resistant plastic (e.g. polycarbonate) and may optionally include one or more anti-fog or glare reducing coatings or treatments. Front lens 25 includes a front surface 26 and an opposed rear surface 27 either of which may carry a treatment T. A gasket 28 is positioned adjacent to rear surface 27 proximate to the periphery of front lens 25. Gasket 28 may be secured to rear surface 27 using a pressure sensitive adhesive (PSA) or other suitable adhesive material. A rear lens 29 abuts gasket 28 and is also constructed of plastic that may be composed of a shatter resistant plastic (e.g. polycarbonate). As is evident from FIGS. 2 and 2A, the outer shape of rear lens 29 is sized differently and may be somewhat smaller than that of front lens 25. Rear lens 29 includes a front surface 30 and a rear surface 31 either of which may include optional anti-fog or glare reducing coatings or treatments designated by the capital letter T. Although the treatments T are shown on only a portion of a carrying lens surface, it will be appreciated that the treatment is provided over a substantial portion of the carrying lens surface.

The front surface 30 is spaced from and faces the rear surface 27 of the front lens 25. A liquid crystal device 32 is disposed on front surface 30 of rear lens 29 and is thus positioned between front lens 25 and rear lens 29. It should be appreciated when viewing the figures that, for the purposes of clarity, the relative sizes of individual components may not be to scale. Specifically, liquid crystal device 32 may be described as a very thin layer and thus may be thinner than shown in FIGS. 2 and 2A. And it will further be appreciated that although the liquid crystal device is shown adjacent the front surface of the rear lens, the device may be positioned adjacent any of the other front or rear lens surfaces.

Front frame 11 includes an external lip 35 along substantially the entire periphery thereof so as to define the aperture 12. An internal lip 36 is spaced from external lip 35 by a joining surface 37. Lip 35, lip 36 and joining surface 37 form a peripheral channel 38 which receives and secures front lens 25 therein. As is evident from FIG. 2, rear lens 29 is positioned outside and rearward of channel 38 and is therefore secured within goggles 10 by other means, as will be described later in more detail.

Referring now to FIGS. 3-6, it can be seen that the liquid crystal device 32 is a multi-layer composite structure which includes a first substrate 40a and an opposed second substrate 40b. Substrates 40a and 40b are generally flat sheets of flexible thermoplastic polymer with a peripheral shape which substantially matches that of rear lens 29. A first conductive or electrode layer 41a is disposed on an inner surface of first substrate 40a and a second conductive or electrode layer 41b is disposed on an inner surface of second substrate 40b. Electrode layers 41a and 41b are electrically conductive and may be formed from materials such as indium tin oxide, conducting polymer, or the like. A first alignment layer 42a may be provided on an inside surface of electrode layer 41a and likewise a second alignment layer 42b may be provided on an inside surface of electrode layer 41b. Alignments layers 42a and 42b are provided to control the orientation of liquid crystal materials disposed between the substrates. Substrates 40a and 40b define an inner volume 43, within which is provided a liquid crystal mixture 44. Spacers 45 are provided between substrates 40a and 40b to prevent the collapse of volume 43 and maintain a uniform distance between the facing electrode layers. Spacers 45 are constructed of a material that is more rigid than the substrate material and selected such that the desired optical qualities are maintained. It is believed that spacers 45 may be sized anywhere between about 3 microns to about 20 microns to achieve optimal results.

As is known in the art, the liquid crystal mixture 44 may contain liquid crystals, dyes, photochromic, dichroic, photoelectric, guest-host combinations, and other materials or any combination of those materials which may affect optical performance. Although the mixture 44 may be a fluid, it will be appreciated that it could be in the form of a film or solid with liquid crystal materials dispersed therethrough. The liquid crystal mixture 44 is actuated by the application or variation of an electric potential across the volume 43. However, it will be appreciated that some liquid crystal materials change optical performance upon exposure to other stimuli such as ultraviolet light. In any event, electrical potential is created by causing appropriate charges to accumulate on electrode layers 41a and 41b. When no electric potential is provided across volume 43, the liquid crystals align in a first orientation. When an electric potential is provided, the liquid crystals align in a second orientation. This change in liquid crystal orientation causes the optical characteristics of the liquid crystal device to change. Specifically, the first liquid crystal orientation may result in a lens which is substantially clear and the second liquid crystal orientation may cause the lens to become tinted or darkened. Thus, the liquid crystal device may selectively become tinted. This is advantageous as a user may choose the amount of tint depending upon outdoor conditions, i.e. a tint may be generated in full sun conditions and removed in clouded conditions. This change in orientation may also be used to polarize, reflect, absorb, refract or otherwise alter a characteristic of the impinging light for benefit of the person wearing the goggle.

Figure 4:
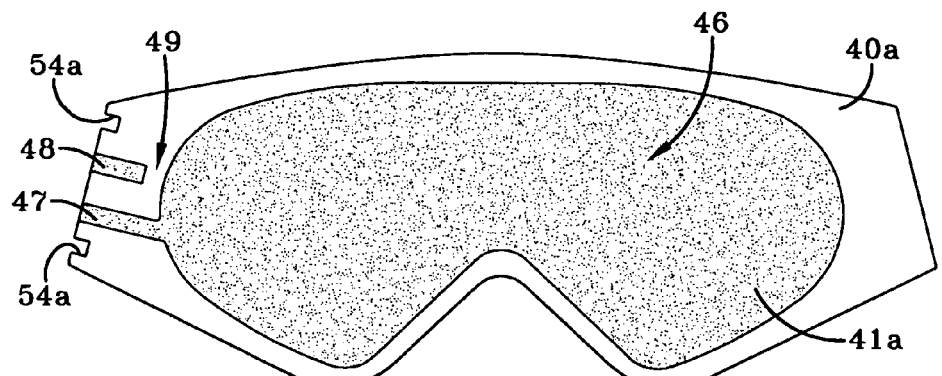
FIG. 4 is an elevated view of a first substrate and a first electrically conductive layer of the liquid crystal device.

Referring to FIG. 4, first electrode layer 41a is shown disposed on first substrate 40a. It can be seen that first electrode layer 41a is not disposed over the entire surface of first substrate 40a, but in a pattern defining an active area 46 and a first and second tab portion 47 and 48. Indeed, the pattern of the active area 46 substantially matches the periphery of the substrate 40a, but is somewhat reduced in size so as to form a border around the active area, except where interrupted by the tab portions 47 and 48. The tab portions 47 and 48 extend substantially all the way to an edge of the substrate, and are aligned substantially parallel to each other in a spaced apart relationship. Second tab portion 48 includes a break 49 wherein no electrode layer is present. In other words, no electricity can be conducted between second tab portion 48 and active area 46.

Figure 5:
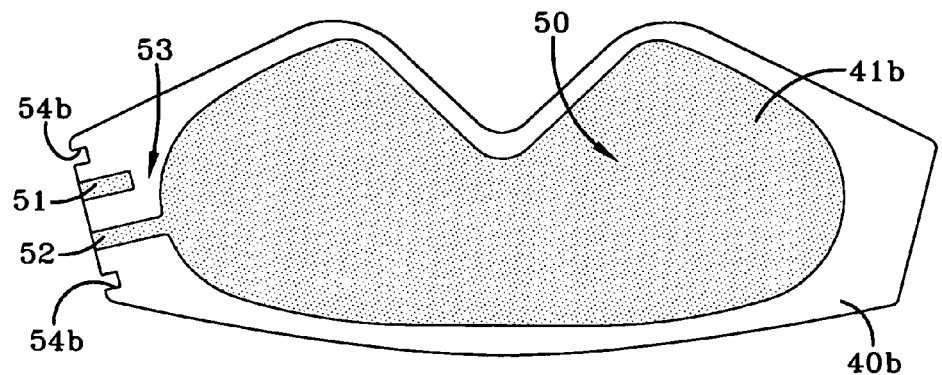
FIG. 5 is an elevated view of a second substrate and a second electrically conductive layer of the liquid crystal device.

Referring now to FIG. 5, second electrode layer 41b is shown disposed on second substrate 40b. It can be seen that second electrode layer 41b is likewise not disposed over the entire surface of second substrate 40b, but in a pattern defining an active area 50 and a first and second tab portions 51 and 52. As with the other substrate, the pattern of the active area 50 substantially matches the periphery of the substrate 40b, but is somewhat reduced in size so as to form a border around the active area, except where interrupted by the tab portions 51 and 52. The tab portions 51 and 52 extend substantially all the way to the edge of the substrate, and are aligned substantially parallel to each other in a spaced apart relationship. First tab portion 51 includes a break 53 wherein no electrode layer is present. In other words, no electricity can be conducted between first tab portion 51 and active area 50. Both substrates 40a and 40b have a pair of corresponding registration notches 54a and 54b along an edge thereof.

Figure 6:
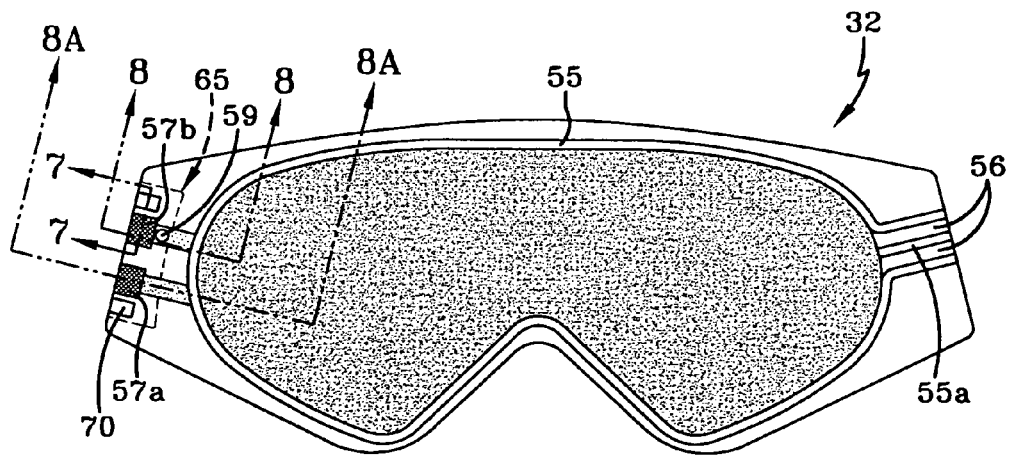
FIG. 6 is an elevated view of a rear lens and liquid crystal device which form part of a sub-assembly of the goggle.

Referring now to FIG. 6, the complete liquid crystal device 32 is shown assembled and secured to rear lens 29. An adhesive bead 55 is disposed between substrates 40a and 40b along the border area that substantially surrounds active areas 46 and 50 so that the active areas face one another. Bead 55 may be an adhesive that is compatible for use with the thermoplastic polymer material of the substrates. Bead 55 defines the outer periphery of volume 43. In other words, bead 55 acts as a seal which contains liquid crystal mixture 44 substantially between active areas 46 and 50 defined on substrates 40a 40b. Ends of the adhesive bead 55, and an adhesive bead 55a create a pair of channels 56 that extend to the edge of liquid crystal device 32. Channels 56 provide a pathway to fill volume 43 with the liquid crystal mixture.

As seen in FIG. 6, the substrates are positioned adjacent one another in an overlapping manner so that tabs 47 and 51 overlap one another and tabs 48 and 52 overlap one another and all extend to the edge of liquid crystal device 32. The position of the substrates 40a and 40b also results in the alignment of registration notches 54a and 54b with one another. The purpose of the registration notches 54 will be discussed in detail later. In any event, the tabs provide an electrical path to active areas 46 and 50 and thus allow selective actuation of the liquid crystal device 32. To that end, a pair of thin copper strips 57a and 57b are positioned between the substrates 40a and 40b so as to connect and interface with the respective tabs and provide a point of electrical connection for a power supply. The thickness of the strips 57a and 57b, which may be provided with an electrically conductive adhesive on one or both sides, is selected to be compatible with the various layers and components of the liquid crystal device 32.

Figure 7:
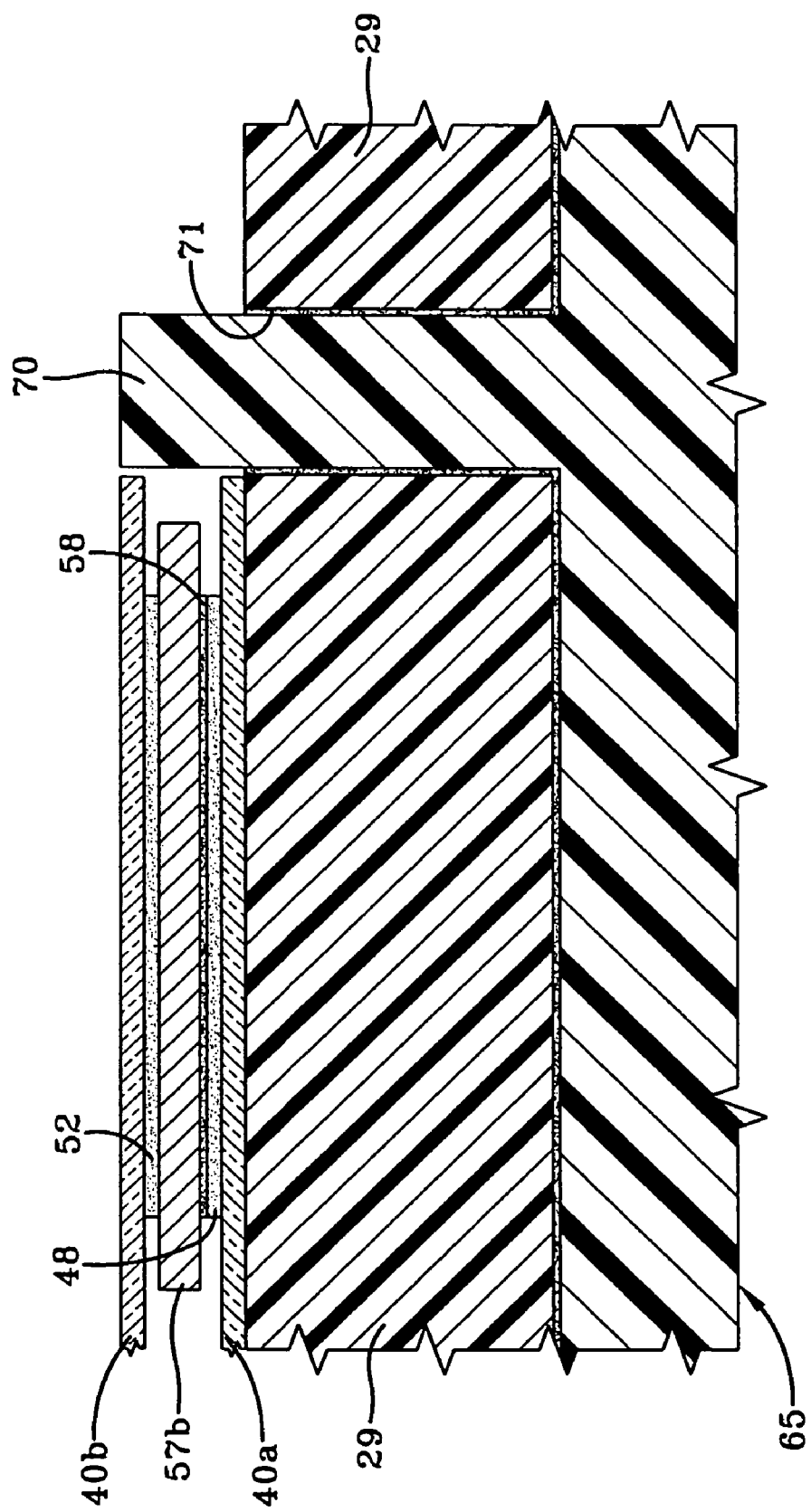
FIG. 7 is a cross-sectional view taken along lines 7-7 of FIG. 6, showing a support, a copper strip, the rear lens and the liquid crystal device assembled to one another according to the present invention.
Figure 8:
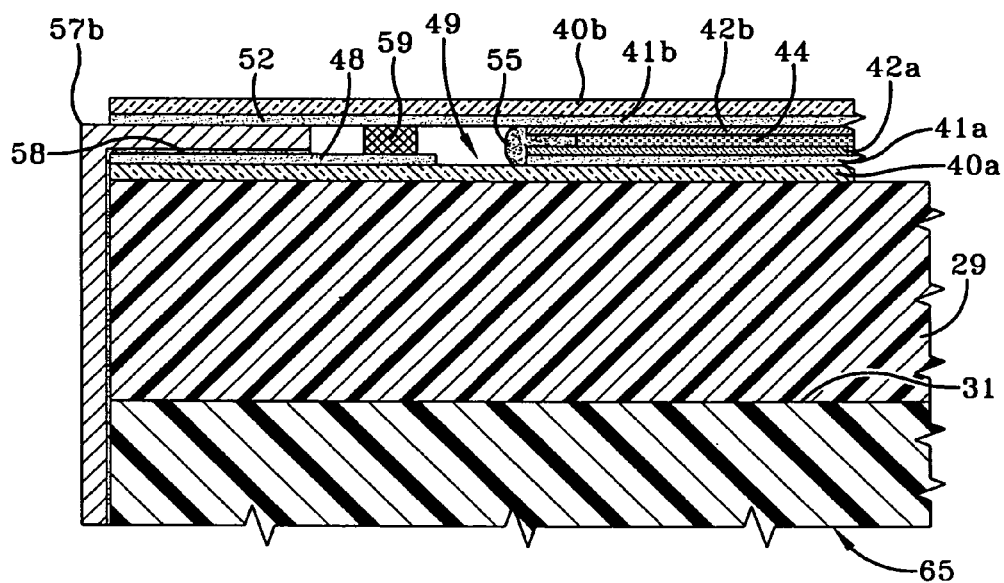
FIG. 8 is a cross-sectional view along lines 8-8 of FIG. 6, showing the support, the copper strip, the rear lens and the liquid crystal device assembled to one another.

Referring now to FIGS. 6, 7 and 8, it can be seen that the device 32 may be positioned adjacent the rear lens 29. Specifically, as seen in FIG. 7, it can be seen that copper strip 57b is secured between tab 48 of first substrate 40a and tab 52 of second substrate 40b. An electrically conductive adhesive 58 may be provided on the bottom surface of copper strip 57b to secure the strip within liquid crystal device 32. In this manner, an electrical connection is formed between copper strip 57b and the electrode layer 41b. In other words, an electric connection is established between copper strip 57b, through tab 52 and finally to active area 50. Conversely, while strip 57b does contact tab 48, no electric connection is realized between strip 57b and second electrode layer 41a because of break 49. However, because conductive adhesive 58 provides an improved electrical connection with bottom tab 48, a cross-over dot 59 may be provided which electrically connects tab 48 to tab 52 to ensure proper electrical connection to and activation of the active area 50.

Figure 8A:
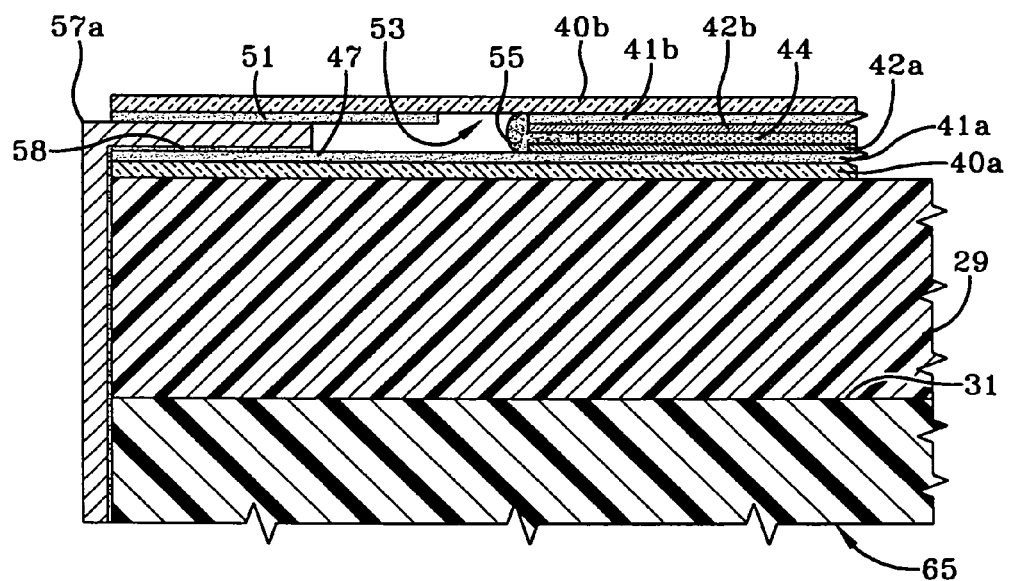
FIG. 8A is a cross-sectional view taken along lines 8A-8A of FIG. 6, showing the support, a second copper strip, the rear lens and the liquid crystal device assembled to one another.
Figure 9:
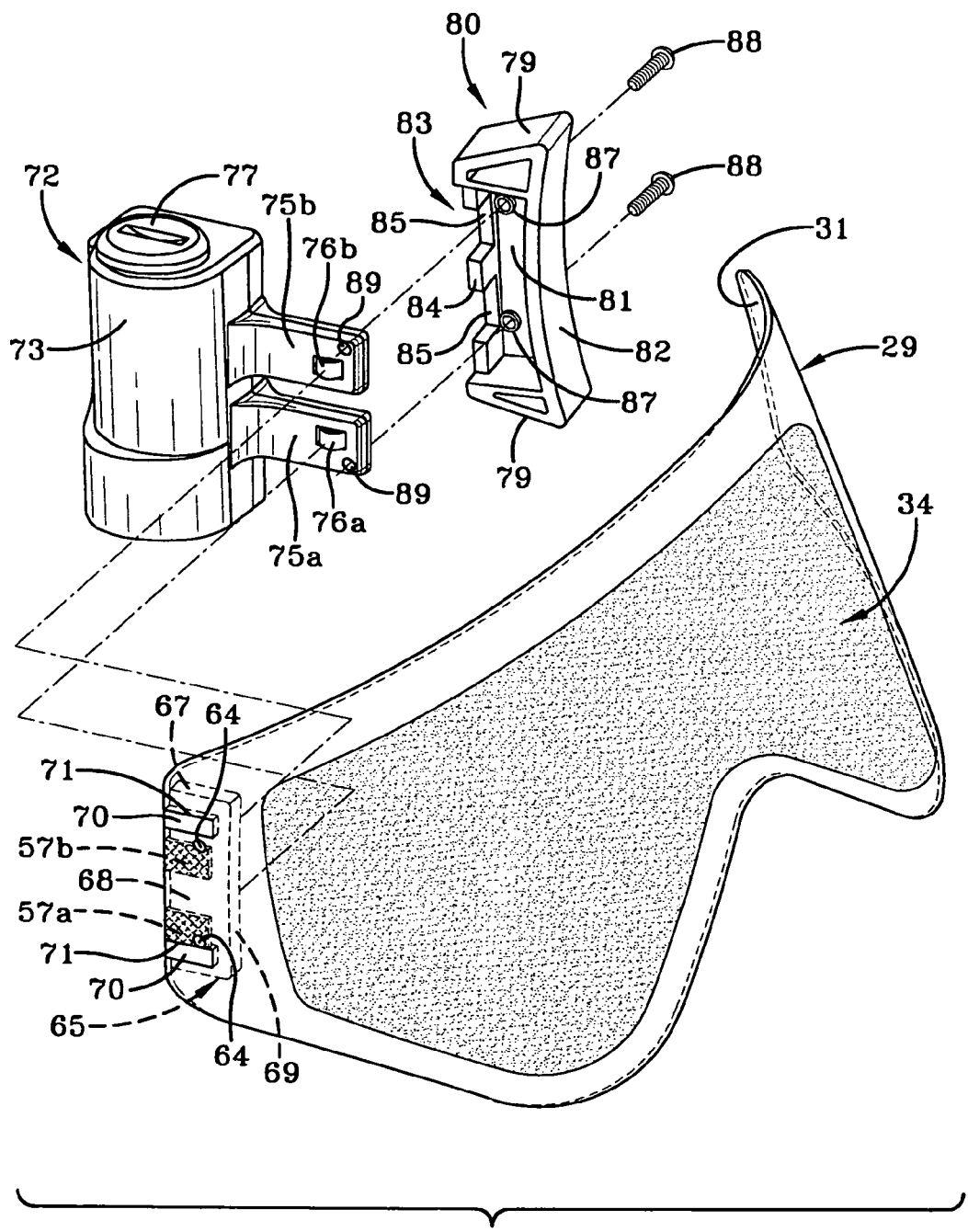
FIG. 9 is a front exploded perspective view of the sub-assembly including the rear lens, the liquid crystal device, a power unit and a power unit retainer according to the present invention.

Referring now to FIGS. 6 and 8A, copper strip 57a is secured between tab 47 of first substrate 40a and tab 51 of second substrate 40b. An electrically conductive adhesive 58 may be provided on the bottom surface of copper strip 57a to secure the strip within liquid crystal device 32. Also, because adhesive 58 is electrically conductive, it promotes electrical connection with the underlying tab 47. As above, break 53 prevents electric connection between copper strip 57a and electrode layer 41b. Electric connection is however achieved between strip 57a and its conductive adhesive 58, and electrode layer 41a via tab 47. Thus, in light of the foregoing it should be evident that copper strip 57a is in electrical communication with first electrode layer 41a, and may therefore energize active area 46.

As best seen in FIGS. 6-10, a support 65 is secured to rear surface 31 of rear lens 29 proximate to copper strips 57. Support 65 is adapted to carry strips 57*a* and 57*b* and provide a rigid base to enable electrical coupling to a power source. Support 65 may be generally rectangular and includes a rear surface 67, an opposed front surface 68 and a plurality of side surfaces 69. One or more side surfaces 69 may be curved to enable unencumbered vision through aperture 12. Support 65 includes a pair of holes 64 which are aligned with corresponding holes 89 on prongs 75 and holes 87 on power unit retainer 80. Each hole 64, while not threaded, is adapted and sized to receive a screw 88 and engage the threads of the screw. A pair of projections 70 extend from front surface 68 and are received in corresponding registration notches 54*a* and 54*b*, and in slots 71 provided by rear lens 29. The interaction between projections 70, notches 54*a*,*b* and slots 71 position support 65 relative to rear lens 29. Copper strips 57 extend from a side edge of liquid crystal device 32, and follows the contour of side surface 69 which is aligned with the lens 29 and device 32, and rear surface 67 in a "C" shaped orientation. In other words, copper strips 57 are bent over outer peripheral side surface 69 and again bent over rear surface 67 to closely form to support 65. Adhesive 58, which is disposed on substantially the entire bottom surface of copper strips 57, causes strips 57 to adhere to support 65. Further, an adhesive may be provided between front surface 68 and rear lens 29 to further secure support 65 to rear lens 29.

Liquid crystal device 32 is selectively actuated by a power unit 72. Power unit 72 includes a housing 73 which contains a battery and circuitry which will be described later in more detail. The battery is retained by a threaded cover 77 secured to the housing 73. A state change button 74 is provided on a bottom surface of housing 73, actuation of which causes the selective actuation of liquid crystal device 32. A first prong 75*a* extends from housing 73 and includes a first conductive lead 76*a*. A second prong 75*b* extends from housing 73—in the same general direction and orientation as prong 75*a*—and includes a second conductive lead 76*b*. Leads 76*a* and *b* are adapted to contact copper strips 57*a* and *b* respectively. Leads 76 may be comprised of a resilient material or may be spring loaded to ensure proper electrical contact when pressed against copper strips 57. Although a pair of prongs are shown, it will be appreciated that a single prong could be used as long as the leads are electrically isolated from one another. Thus, an electrical circuit is completed when leads 76 are engaged with copper strips 57 and, in turn, the electrode layers of the liquid crystal device 32.

As seen in FIGS. 9-11A, a power unit retainer, designated generally the numeral 80, is provided and sized to fit flush against framework 17 between front and rear frames 11 and 18. Power unit retainer 80 includes a wall 81 and a curved side wall 82 extending from wall 81 toward framework 17. A pair of flattened side walls 79 extend from the ends of curved side wall 82 and to define an open side 83. Open side 83 includes a notched wall 84 defining a pair of notches 85. Notches 85 are adapted to receive and secure prongs 75 therein, as will be hereinafter described.

As best seen in FIGS. 11 and 11A, when assembled, prongs 75 are received in a pair of retaining holes 86 provided in a side of framework 17 proximal one of the strap retainers 14. Once inserted, leads 76*a* and 76*b* face forwardly and bear against copper strips 57*a* and 57*b* respectively. When the goggle 10 is fully assembled, rear lens 29, which carries the liquid crystal device 32, and support 65, which is secured to both the lens 29 and device 32, are thus positioned between prongs 75 and gasket 28 of front lens 25. Power unit retainer 80 is then installed so that prongs 75 reside within notches 85.

Rear wall 81 of power unit retainer 80 includes a pair of holes 87 which are each adapted to receive a screw 88 without engaging the threads of said screw. Each prong 75 has a hole 89 which is aligned with a corresponding hole 87 on power unit retainer 80. Holes 89, while not threaded, are adapted to receive a corresponding screw 88 and engage the threads thereof. Screws 88 are received in holes 87 of power unit retainer 80, holes 89 on prongs 75 and holes 64 in support 65. In this manner, power unit 72 is secured to framework 17 and removal through retainer holes 86 is prevented. Prongs 75 thereafter prevent rearward movement of rear lens 29, thereby securing one side of rear lens 29 within goggle 10. Additionally, proper alignment of leads 76*a* and 76*b* with respect to copper strips 57*a* and 57*b* is established and rotation of prongs 75 with respect to support 65 is prevented.

Figure 12A:
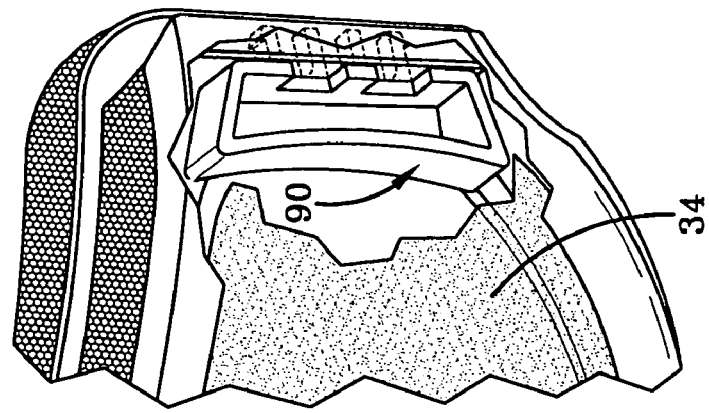
FIG. 12A is a partial perspective view of the retaining clip in the goggle frame with the lenses partially broken away.
Figure 12:
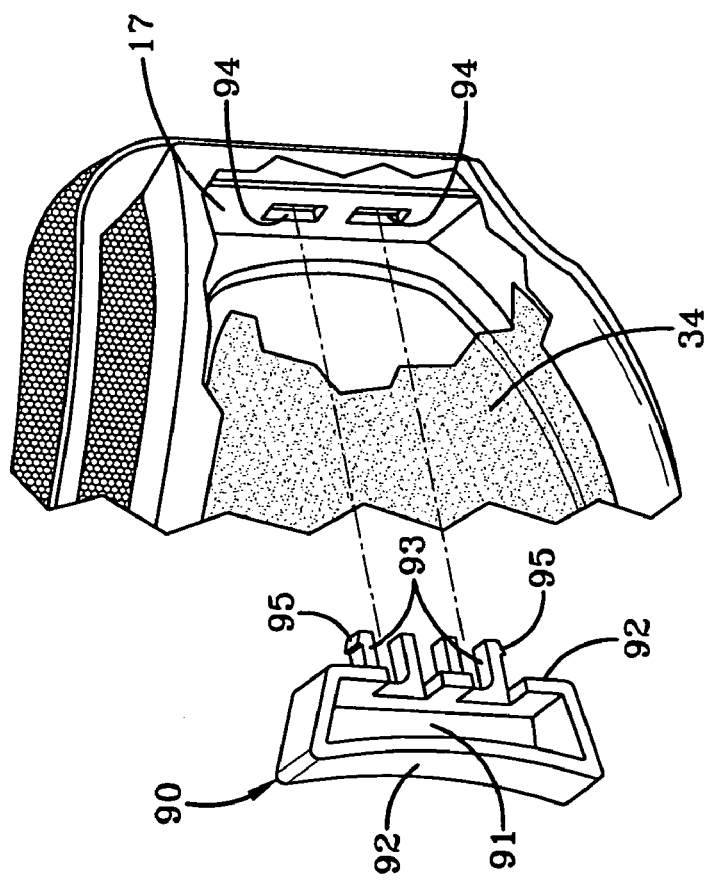
FIG. 12 is a partial exploded perspective view showing the retaining clip and the goggle frame with the lenses partially broken away.

Referring now to FIGS. 12 and 12A, a retaining clip, generally designated by the numeral 90, is adapted to secure and position the other side of rear lens 29 within goggle 10. Retaining clip 90 includes a rear wall 91 and side walls 92 extending forwardly therefrom. Retaining clip 90 is shaped to fit flush with framework 17 and between front and rear frames 11 and 18. A pair of deflectable resilient clips 93 are provided which extend inward from sidewall 92 toward framework 17. Framework 17 includes a pair of retaining holes 94 which are sized to receive clips 93. Clips 93 include hook portions 95, which are deflected by a framework 17 until fully inserted in the holes 94. Once fully inserted, the hook portions 95 prevent movement of the clip 90 with respect to the framework 17. In this manner, retaining clip 90 prevents rearward movement of rear lens 29, thereby securing the other side of rear lens 29 within goggle 10.

To summarize, the goggle components are assembled in the following manner, although it will be appreciated that the assembly steps could be re-ordered depending upon the positioning of the liquid crystal device with respect to the lenses and other considerations. First, the gasket 28 is adhered to the rear surface 27 of lens 25 forming a first sub-assembly. Next, a second sub-assembly which includes the rear lens 29, the liquid crystal device 32, and the attached support 65, is positioned next to the first sub-assembly (gasket 28 and lens 25). Then, while being held together, both sub-assemblies are positioned within the frame 11. The lens 25 is then inserted into the channel 38 and held in place by the lips 35 and 36. The second sub-assembly (lens 29, device 32 and support 65) is somewhat received by the frame and contacts the gasket 28, but is not secured to the frame, the gasket 28 or the lens 25. Next, the prongs of the power unit 72 are inserted into the retaining holes 76. The retainer 80 is then fastened to the prongs with the screws 88 to hold the power unit in place so as to prevent inadvertent withdrawal from the frame. The support 65 is also fastened with the screws 88 to the prongs to maintain electrode alignment. The retainer 80 also functions to cover the strips 57*a* and 57*b*, and holds one side of the second sub-assembly in place. Next, the retaining clip 90 is secured to the other side of the frame 17. Specifically, the resilient clips 93 are inserted into holes 94 and retain the other side of the sub-assembly.

It should be appreciated that the aforementioned configuration significantly reduces stresses applied to liquid crystal device 32 as compared to prior art methods. Specifically, rear lens 29, which carries liquid crystal device 32, is restricted in forward movement by gasket 28 and/or second lip 36. Side movement is restricted by second lip 36 and/or framework 17. Finally, rearward movement is restricted by power unit retainer 80 and retaining clip 90. Thus, the rear lens is securely retained within the frame 11. However, since the rear lens 29 is not secured to the gasket or the frame, it is free to "float" within these confines. This floating configuration results in reduced stress and consequently a lower incidence of liquid crystal device failure.

Figure 13:
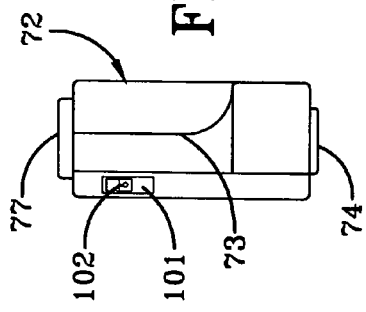
FIG. 13 is a rear elevational view of the power unit according to the present invention.
Figure 14:
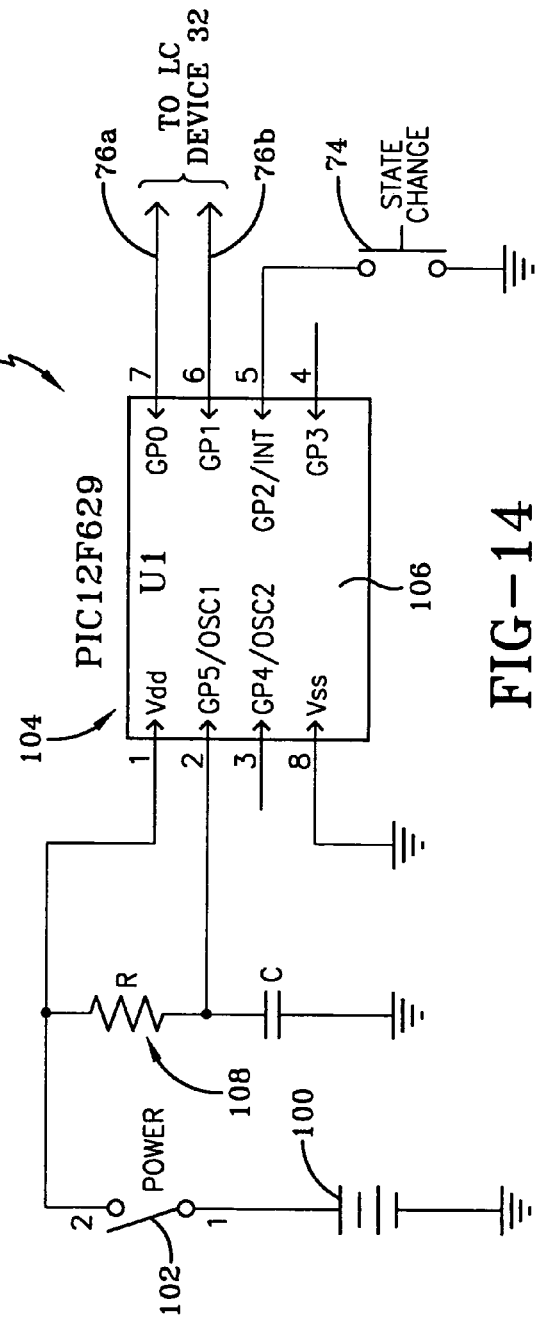
FIG. 14 is a schematic view of a power circuit carried by the power unit used with the goggle's liquid crystal device according to the present invention.

Referring now to FIGS. 13 and 14, it can be seen that the power unit 72 includes a housing 73 which provides a state change switch 74. Additionally, a battery cover 77 retains a battery 100 within the housing 73. A side of the housing 73, which is opposite the side from which the prongs 75 extend, provides a recess 101. Within this recess is provided a power switch 102 which functions as a master power switch.

As best seen in FIG. 14, the power unit 72 includes a drive circuit 104 that controls the liquid crystal device 32. As can be seen from the circuit 104, the battery 100 is connected between ground and the master power switch 102. When the switch 102 is closed, power is supplied to a processor 106 which is a programmable micro-controller adapted for use with the liquid crystal device 32. Power is also supplied to a resistor-capacitor network 108 which provides an input to the processor 106 so as to provide an appropriate clock frequency to drive the processor. In this embodiment, the processor is run at about a 30 kHz frequency; however, other compatible frequencies could be utilized. In any event, the state change switch 74 is also connected to the processor 106 so as to allow for actuating the liquid crystal device. It will be appreciated that the master power switch 102, when in an on condition, maintains constant application of power to enable operation of the state change switch 74. This allows for actuation of the liquid crystal device to its different operational states via the leads 76a and 76b connected to output terminals of the processor 106. However, when the ski goggle is not to be used, such as when the user is traveling or the like, the master power switch can be turned off so as to prevent unwanted power drain, thus preserving the life of the battery. It will also be appreciated that the power unit 72 is configured with respect to the goggle such that the state change switch 74 is oriented in a direction other than adjacent a top edge or surface of the goggle. This is done so that the state change switch is not inadvertently actuated by pressing against a lower edge of a helmet. Accordingly, the possibility of unwanted actuation of the state change switch is avoided.

Based upon the foregoing, it will be appreciated that the goggle described herein has a number of advantageous features. First, the goggle is advantageous inasmuch as the liquid crystal device 32 carried by the goggle is structured to withstand the rigors of use in a skiing application or other environment exposed to extremes in temperature and potentially harsh environmental conditions. In particular, the liquid crystal device is constructed so as to be adaptable to make power connections without the use of thin lead wires. Indeed, the liquid crystal device is provided with relatively wide electrode tabs that are suitable for connection to copper strips that are connected to spring-loaded leads of a power unit. Moreover, the power unit is constructed so as to be adaptable for use with a ski goggle or other related eyewear without being unduly cumbersome or obtrusive to the wearer of the goggle. Moreover, the construction allows for the liquid crystal device to be retained in such a manner so that stresses normally associated with the lenses of a ski goggle frame do not adversely affect the operation of the liquid crystal device. In other words, the lens which supports the liquid crystal device is allowed to somewhat float within the goggle frame so that normally applied stresses are not applied to the liquid crystal material and associated substrates.

Still another advantage of the present invention is that the power unit is allowed to be fairly easily removed from the goggles, such that it can be replaced in the event the processor or associated circuitry is rendered inoperative or, in the alternative, the lens supporting the liquid crystal device can be replaced if the liquid crystal device is found to be defective.

Yet another advantage of the goggle is that the power unit utilizes a master switch which is recessed so as to prevent unwanted power drain when the goggle is not desired to be used. It is also advantageous that the power switch, when in an on condition, allows for easy access to the state change switch which triggers a change in the tint or optical performance of the liquid crystal device 32.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto and thereby. Accordingly, for an appreciation of the true scope and breadth of the invention, reference should be made to the following claims.

What is claimed is:

1. A goggle comprising:
   a frame defining an aperture, said frame providing a peripheral channel about said aperture;
   a lens assembly comprising a front lens, a rear lens spaced apart from said front lens and a liquid crystal device disposed on only one of said lenses; and
   wherein said peripheral channel receives only the other one of said lenses which does not carry said liquid crystal device, and wherein the other one of said lenses not carrying said liquid crystal device is spaced apart from said liquid crystal device.

2. The goggle according to claim 1, wherein said lens assembly further comprises a gasket, said front lens having a front surface and a rear surface, said rear lens having a front surface and a rear surface, said gasket being disposed on said rear surface of said front lens and said liquid crystal device being disposed on said front surface of said rear lens.

3. The goggle according to claim 2, wherein said gasket is adhered only to said front lens.

4. The goggle according to claim 1, wherein said rear lens has an outer periphery different than an outer periphery of said front lens.

5. The goggle according to claim 1, further comprising:
   a power unit including a housing from which extends at least one prong, said frame including at least one first retaining hole, each said prong being received in one said first retaining hole, said prongs retaining said lens assembly in said frame.

6. The goggle according to claim 5, further comprising:
   a retaining clip including at least one deflectable clip and said frame including at least one second retaining hole opposed from said at least one first retaining hole, said at least one deflectable clip being receivable in said at least one second retaining hole, said retaining clip retaining said lens assembly in said frame.

7. The goggle according to claim 5, further comprising:
   a power unit retainer including at least one notch, said at least one notch receiving said at least one prong therein, wherein said power unit retainer is coupled to said at least one prong to retain said power unit to said frame.

8. The goggle according to claim 5, further comprising:
   a support secured to said rear lens, a pair of conductive strips electrically connected to said liquid crystal device, said at least one prong, a pair of electric leads, wherein said conductive strips extend from the edge of said liquid crystal device, and are carried by said support; each said electric lead contacting a corresponding one of said conductive strips.

9. A liquid crystal lens assembly for a goggle, comprising:
a lens adapted to fit within the goggle, said lens having a front surface and a rear surface;
a liquid crystal device disposed on one of said surfaces and including opposed first and second substrates, said first substrate having a first conductive layer disposed thereon, said first conductive layer including a first active area and first and second tabs, said second substrate having a second conductive layer disposed thereon, said second conductive layer including a second active area and third and fourth tabs, said first and second active areas being aligned and defining a volume therebetween to receive a liquid crystal material;
a first conductive strip disposed between said first and third tabs;
a second conductive strip disposed between said second and fourth tabs; and
wherein said first conductive strip is electrically connected to said first active area and said second conductive strip is electrically connected to said second active area.

10. The liquid crystal lens assembly according to claim 9, wherein said second tab includes a break preventing electrical conductivity between said second tab and said first active area and said third tab includes a break preventing electrical conductivity between said third tab and said second active area.

11. The liquid crystal lens assembly according to claim 9, wherein said first and said second conductive strips are composed of a metallic material.

12. The liquid crystal lens assembly according to claim 9, wherein said first and said second conductive strips include an electrically conductive adhesive disposed on at least one surface.

13. The liquid crystal lens assembly according to claim 12, further comprising an electrically conductive cross-over dot electrically connecting said second and said fourth tabs.

14. The liquid crystal lens assembly according to claim 9, further comprising a support having a front surface and a rear surface, said front surface being secured to said rear surface of said lens proximate said tabs, said first and said second conductive strip extending from said liquid crystal device and carried by said support to said rear surface.

15. The liquid crystal lens assembly according to claim 14, further comprising a power unit including a first and second lead, said first lead contacting said first conductive strip and said second lead contacting said second conductive strip.

16. The liquid crystal lens assembly according to claim 15, wherein said power unit includes a housing and a first and second prong, said first prong carrying said first lead and said second prong carrying said second lead.

17. The liquid crystal lens assembly according to claim 14, wherein said lens includes a pair of slots and said support includes a pair of projections, said projections being received in said slots to position said support on said lens.

18. A goggle comprising:
a frame defining an aperture, said frame having a top edge;
a lens assembly received within said aperture and comprising a front lens, a rear lens spaced apart from said front lens and a liquid crystal device disposed on said rear lens, wherein the front lens is spaced apart from the liquid crystal device; and
a power unit electrically connected to said liquid crystal device including a housing positioned outside said frame and a state change button, wherein said state change button is depressible to actuate said liquid crystal device, and wherein said state change button is positioned away from said top edge.

19. The goggle according to claim 18, wherein said frame has a bottom edge opposite said top edge, wherein the goggle is normally worn in such a way that said bottom edge is proximally aligned in a position below the user's eyes and said top edge is proximally aligned in a position above the user's eyes.

20. The goggle according to claim 18, wherein said power unit further comprises a master switch, wherein said master switch must be in an on position for said state change button to actuate said liquid crystal device.

21. The goggle according to claim 18, wherein the liquid crystal device is disposed on a front surface of said rear lens.

22. The goggle according to claim 18, wherein said frame provides a peripheral channel about said aperture wherein said peripheral channel receives only the front lens.

23. The goggle according to claim 18, wherein said front lens and rear lens are plastic.

* * * * *